(12) United States Patent
Javors

(10) Patent No.: US 10,918,399 B1
(45) Date of Patent: Feb. 16, 2021

(54) METHODS AND SYSTEMS FOR FEMORAL CONDYLAR RESECTION ARTHROPLASTY OF THE KNEE

(71) Applicant: Jonathan R. Javors, Dyer, IN (US)

(72) Inventor: Jonathan R. Javors, Dyer, IN (US)

( * ) Notice: Subject to any disclaimer, the term of this patent is extended or adjusted under 35 U.S.C. 154(b) by 500 days.

(21) Appl. No.: 15/464,241

(22) Filed: Mar. 20, 2017

Related U.S. Application Data

(63) Continuation-in-part of application No. 15/427,016, filed on Feb. 7, 2017, now Pat. No. 10,426,504.

(51) Int. Cl.
*A61F 2/38* (2006.01)
*A61B 17/17* (2006.01)
*A61B 17/16* (2006.01)

(52) U.S. Cl.
CPC ...... *A61B 17/1764* (2013.01); *A61B 17/1675* (2013.01); *A61F 2/3859* (2013.01); *A61F 2002/3863* (2013.01)

(58) Field of Classification Search
CPC ...... A61F 2/3859; A61F 2/481; A61F 2/4684; A61F 2002/3863; A61B 17/1764; A61B 17/1675; A61B 17/0206; A61B 17/32093; A61B 1/317

See application file for complete search history.

(56) References Cited

U.S. PATENT DOCUMENTS

| 5,667,481 A | * | 9/1997 | Villalta | A61B 17/02 600/219 |
| 2003/0028196 A1 | * | 2/2003 | Bonutti | A61B 17/025 606/87 |
| 2003/0130665 A1 | * | 7/2003 | Pinczewski | A61B 17/154 606/88 |

* cited by examiner

*Primary Examiner* — Christopher D. Prone
(74) *Attorney, Agent, or Firm* — Charles T. Riggs, Jr.

(57) ABSTRACT

A method and system for femoral condylar resection arthroplasty of the knee, which preserves the undamaged meniscus, whether by arthroscopy arthrotomy, and only replaces the damaged area of the femoral condyle. In one embodiment, only the distal femoral condyle is replaced and the posterior femoral condyle remains intact. In another embodiment, both the distal and posterior femoral condyle are replaced. The method and system include placing an intercondylar insert between articular surfaces of a distal femoral condyle and a tibial plateau with the knee in extension. The method and system also includes a box retractor having four right angle blades, two for medial structures and two for lateral structures. The blades are at two depths, shallow and deep. The components of the system are preferably of plastic material. The method and system preserve the meniscus on top of the tibial plateau.

8 Claims, 7 Drawing Sheets

FIGURE 2A
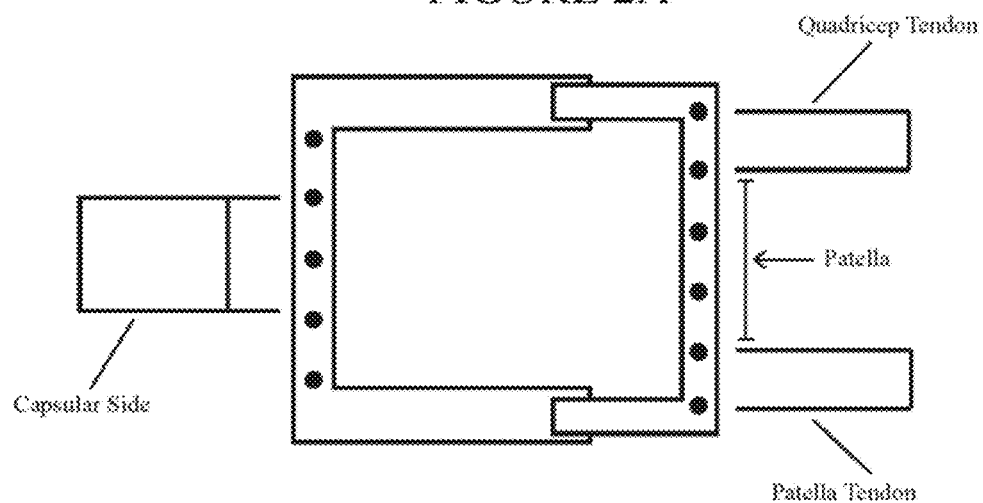
FIGURE 2B
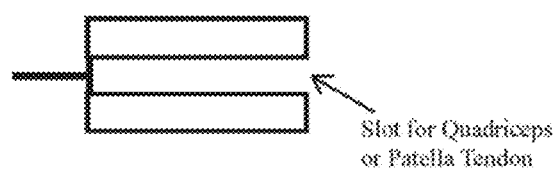
FIGURE 2C

FRONT VIEW

SIDE VIEW

FIGURE 5A
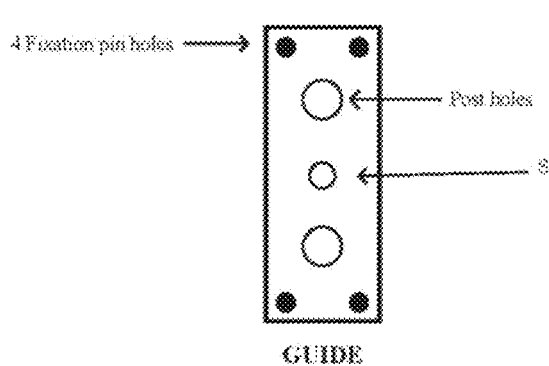
FIGURE 5B
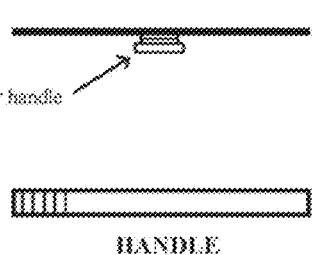
FIGURE 5C
DISTAL FEMORAL CONDYLE TRIAL
*Multiple trial sizes*
FIGURE 5D

DISTAL AND POSTERIOR FEMORAL CONDYLE TRIAL

METHODS AND SYSTEMS FOR FEMORAL CONDYLAR RESECTION ARTHROPLASTY OF THE KNEE

This application is a continuation in part of U.S. patent application Ser. No. 15/427,016 filed Feb. 7, 2019, now U.S. Pat. No. 10,426,504 issued Oct. 1, 2019.

TECHNICAL FIELD

The exemplary teachings herein pertain to methods, systems, components and/or devices for limited arthroscopic assisted resection arthroplasty (LAARA) of the knee, and in particular, to methods, systems and devices for femoral condylar resection arthroplasty (FCRA) of the knee.

BACKGROUND

Since Sir John Charnley pioneered the design and implementation of the total hip arthroplasty in the mid-1960s, joint replacement surgeons and orthopedic product companies have been striving to improve on the original design, often in collaboration. These improvements have been focused on the following goals:
  i) Improvement of patient function
  ii) Ease of insertion, through improved instrument design and surgical approach
  iii) Reproduction of beneficial results, both from the patient and surgeon standpoints
  iv) Longevity of the product
  v) Smaller incisions
  vi) Faster recovery
  vii) Shorter operating time
  iii) multi-modal pain control parameters Over the last fifty years, significant strides have been made in all of these goals. Newer products with improved materials have increased component longevity. Minimally invasive techniques, with multi-modal pain control, standardization of physical therapy protocols, and improved instrument design have all improved patient function and shortened recovery time. Procedures being performed more frequently by surgeons better versed in joint replacement surgery have led to more beneficially reproducible results.

One of the primary goals of all joint replacement arthroplasty techniques and designs, is to remove as little bone as possible to accomplish the above goals. Always in the back of every joint replacement surgeon's mind is the fact that if the patient lives long enough, of if they put undue stress across the joint, whether due to being too active, weight gain, or other factors, the prosthesis will fail. The smaller amount of bone removed at the time of the primary arthroplasty, the less invasive revision necessary.

Unicompartmental arthroplasty of the knee, has been part of the joint replacement surgeons armamentarium for over 15 years. Commonly, only, one of the three compartments in the knee has damage and is symptomatic. The other two are normal. The unicompartmental arthroplasty allows for the removal of the damaged compartment but preserves the patient's normal and native undamaged compartments.

The standard design of the traditional unicompartmental knee arthroplasty (when replacing the medial or lateral compartments) is to replace the distal and posterior condyles of the femur and the articular surface of the tibial plateau of the involved compartment. The meniscus is removed.

Often there is damage to the distal femoral weight bearing surface, yet the posterior femoral condyle and the tibial plateau articular surfaces are unaffected.

The following prior art references relate to and/or discuss one or more of the above described issues, and are each herein fully incorporated by reference: U.S. Patent Application Publication Nos. 2007/0032876 A1 entitled Knee Joint Prosthesis, published on Feb. 8, 2007, and 2008/0132895 A1 entitled Instruments and Method for Arthroscopic Arthroplasty of the Knee, published on Jun. 5, 2008, both by inventor Ron Clark of Valparasio, Ind.

SUMMARY

One or more methods, systems, designs, instruments, implements, components and/or devices for femoral condylar resection arthroplasty (FCRA) of the knee are disclosed. In a preferred embodiment, only the damaged femoral condyle of the knee (medial or lateral; distal and/or posterior, depending on the extent of damage) is replaced. By doing so, the method and system maintains the meniscus and corresponding tibial plateau, while replacing only the damaged surface of the femoral condyle and preserves normal tissue of the meniscus and tibial hyaline cartilage. This would be very beneficial in younger and more active patients. The method and system does not preclude a "traditional" uni-compartmental arthroplasty at some point in the future should that become necessary. The method and system can be performed with limited exposure, post arthroscopy for correction of other intra-articular knee pathology. The surgical time and recovery would be shorter because of the less invasive nature of the procedure.

The one or more methods, systems, designs, instruments, implements, components and/or devices incorporate the following characteristics and/or features:

1) Preserves the undamaged part of the meniscus. All current unicompartmental arthroplasty techniques sacrifice the meniscus. In the procedures disclosed herein, only the torn part of the meniscus is removed in the first part of the process (surgical procedure) via the arthroscope.

2) Only replaces the damaged area of the femoral condyle (distal femoral condyle or both distal and posterior femoral condyle). Whether to replace the distal and/or the posterior femoral condyle is anticipated through careful review of the pre-op MRI, but confirmed at arthroscopy. If there is significant damage to the tibial plateau as seen at arthroscopy, in the pre-operative MRI, or at the time of arthrotomy, then a traditional unicompartmental arthroplasty is performed.

3) While either plastic or metal material for the components may be used, preferably plastic components are used, as plastic articulating on the hyaline cartilage tibial plateau will mimic nature better than metal.

4) Once the arthroscopic procedure is finished, the surgeon will than make a small (2-3 inch) incision, use the box retractor, slide in the intra-compartmental (IC) insert, place on the femoral cutting jig, fix it with pins, make the appropriate distal femoral cut, and cement in the component. If the posterior is to be replaced, a chamfer and posterior cut will be made, using existing cutting blocks.

5) The disclosed procedures may be performed by arthroscopic surgeons, in addition to joint arthroplasty surgeons.

The presently disclosure methods, systems, designs and instruments for femoral condylar resection arthroplasty provide the joint replacement surgeon and/or arthroscopic surgeon two primary options when performing femoral condylar replacement of either the medial or lateral compartments of the knee: 1) Replacement of the distal femoral condyle only, when the posterior femoral condyle and the tibial articular surfaces are both normal. This also allows for the preservation of stable medial meniscal tissue; or 2) Replacement of the entire femoral condyle, both distal and posterior.

Additional advantages and novel features will be set forth in part in the description which follows, and in part will become apparent to those skilled in the art upon examination of the following and the accompanying drawings or may be learned by production and/or operation of the teachings herein.

BRIEF DESCRIPTION OF THE DRAWINGS

The drawing figures depict one or more implementations in accordance with the present teachings, by way of example only, not by way of limitation. In the drawing figures, like reference numerals refer to the same or similar elements.

FIG. 2A is a schematic diagram of a box retractor used in the method(s) and system(s) of present disclosure.

FIG. 2B is a schematic diagram illustrating an anterior view of the box retractor of FIG. 2A.

FIG. 2C is a schematic diagram illustrating the tendon slots of the box retractor of FIG. 2A.

FIGS. 5A-5D are schematic diagrams of trial components used in the method(s) and system(s) of present disclosure, with FIG. 5A depicting a front view of a guide, FIG. 5B depicting a side view of a guide, FIG. 5C depicting a handle, and FIG. 5D depicting a distal femoral condyle trial.

DETAILED DESCRIPTION

The following description refers to numerous specific details which are set forth by way of examples to provide a thorough understanding of the relevant method(s) and system(s) disclosed herein. It should be apparent to those skilled in the art that the present disclosure may be practiced without such details. In other instances, well known methods, procedures, components, instruments, implements and/or devices have been described at a relatively high-level, without detail, in order to avoid unnecessarily obscuring aspects of the present disclosure.

Figure 1:
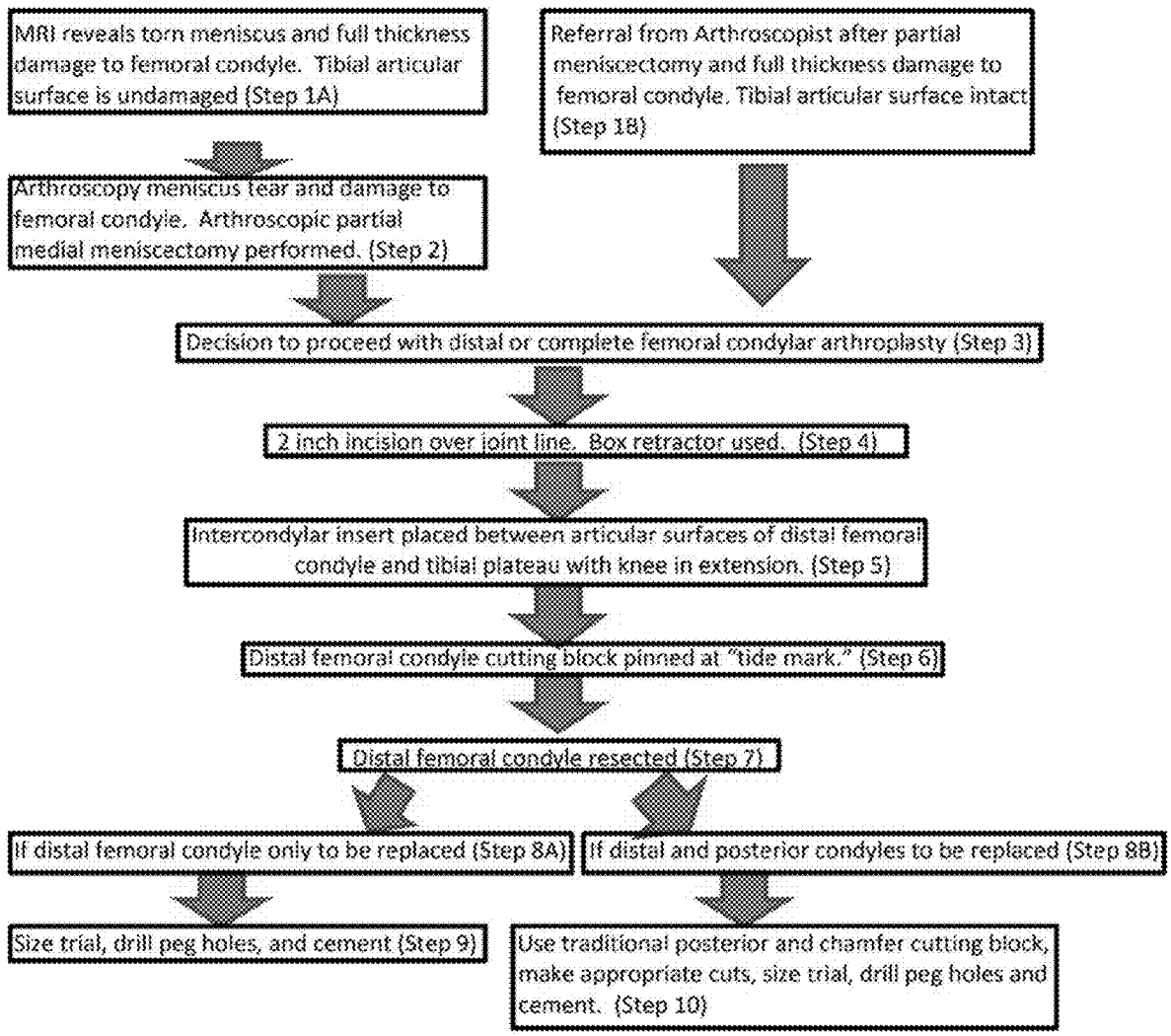
FIG. 1 is a flow chart illustrating the procedure(s) according to the present disclosure.
Figure 3A:
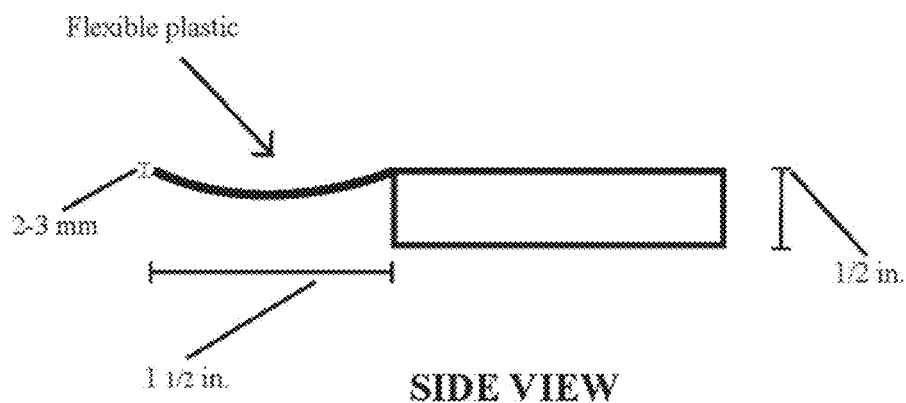
FIG. 3A is a schematic diagram depicting a side view of an intercompartmental (IC) insert used in the method(s) and system(s) of present disclosure.
Figure 3B:
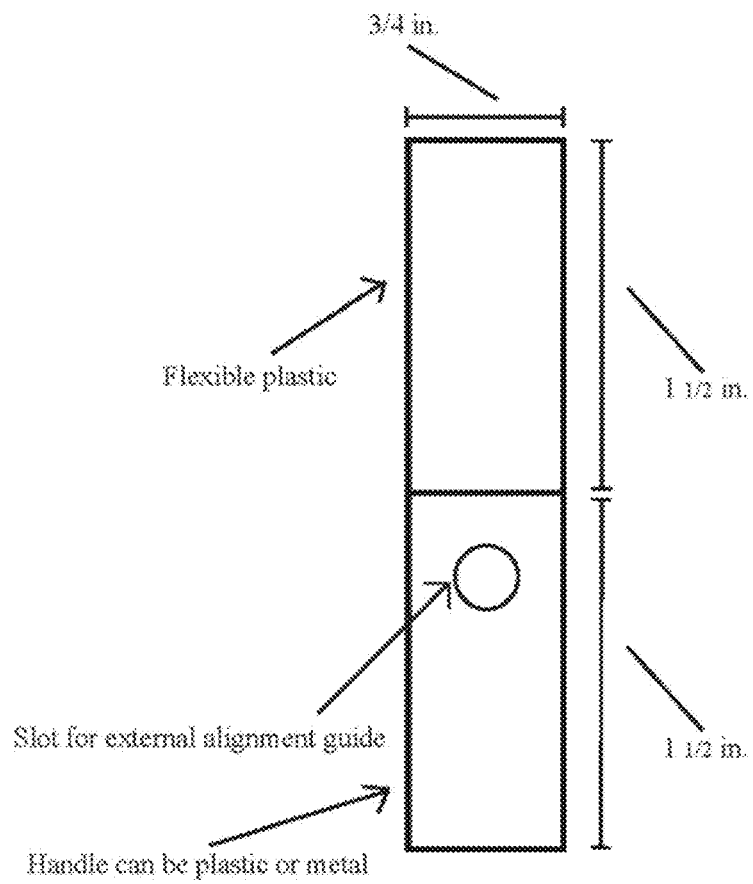
FIG. 3B is a schematic diagram depicting a top view of the intercompartmental (IC) insert of FIG. 3A.
Figure 4A:
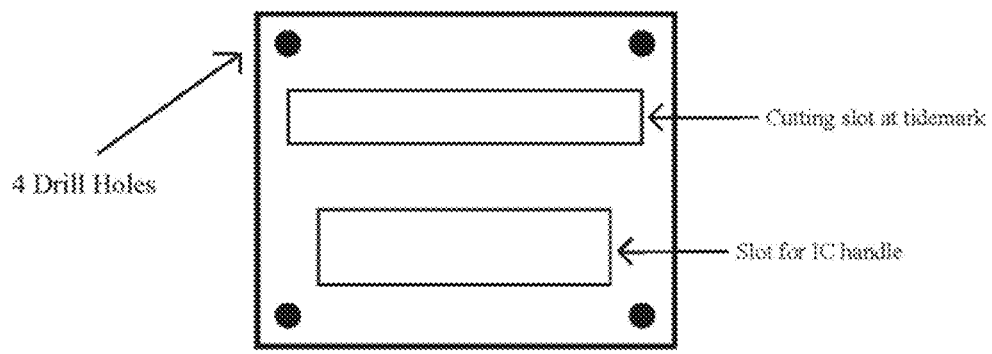
FIG. 4A is a schematic diagram depicting a front view of a cutting block used in the method(s) and system(s) of present disclosure.
Figure 4B:
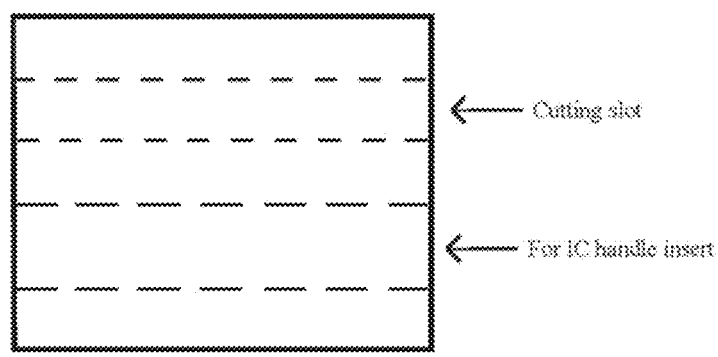
FIG. 4B is a schematic diagram depicting a side view of the cutting block of FIG. 4A.

FIG. 1 is flow chart illustrating the method(s) for the present disclosure for femoral condylar resection arthroplasty of the knee, with reference to the component(s) used during the method(s). Prior to a decision to proceed with distal or complete femoral condylar arthroplasty (FIG. 1, Step 3), an evaluation of a patient's knee must be undertaken (FIG. 1, Step 1A and/or Step 2), or a referral from an Arthroscopist is made (FIG. 1, Step 1B). Once the decision to proceed is made, the method includes the following steps: Step 4—an approximately two inch incision is made over joint line. The box retractor of FIGS. 2A-2C is used. Step 5—the intercondylar insert of FIGS. 3A-3B is placed between articular surfaces of distal femoral condyle and tibial plateau with knee in extension. Step 6—the distal femoral condyle cutting block of FIGS. 4A-4B is pinned at "tide mark." Step 7—the distal femoral condyle resected. Step 8A—if the distal femoral condyle only to be replaced, perform Step 9: size trial, drill peg holes and cement using the trial components of FIGS. 5A-5D. Step 8B—if distal and posterior condyles to be replaced, perform Step 10: use traditional posterior and chamfer cutting block, make appropriate cuts, size trial, drill peg holes and cement using the trial components of FIGS. 5A-5C and 6.

FIGS. 3A and 3B illustrate the intra-compartmental insert (IC Insert). This insert has a curvilinear, pliable plastic surface that will be used for either a LAARA procedure. (The joint replacement surgeon will use his or her preferred system for a traditional unicompartmental replacement). It is 1.5 cm wide. The curvilinear plastic component will be placed in between the tibial and femoral articular surfaces. The handle of the IC Insert will be hard plastic or metal and will contain a hole for placement of the external alignment guide.

FIGS. 4A-4B illustrate the distal femoral cutting block. This block will be attached to the IC Insert. Preferably, there will be neutral cutting slot. By slight angulation of the cutting block, e.g., 1 degree, 2 degree, or 3 degree superior slope, more or less of the distal condyle can be removed. This will allow a slight increased coverage if the distal femoral condyle wear extends slightly into the posterior condyle. However, unless otherwise determined, a neutral cut should be made. An alternate distal femoral cutting block is disclosed in FIGS. 4C-4D, and includes one or more guidewire slot(s) (two shown) through which one or more guidewire(s) can be placed to help line up the bone cut, as discussed in more detail below.

FIGS. 2A-2C illustrate the box retractor. This box retractor is a retractor designed specifically for the LAARA procedure. Since the incision only needs to expose the most inferior aspect of the distal femur and most superior aspect of the tibia, it may be relatively small. However, the patella, the patellar and quadriceps tendon, and the opposite capsular structures must be retracted to allow placement of the instruments and allow visualization of the bone cuts, trial sizing, and then placement of the definitive component. There are four right angle blades (two for medial structures and two for lateral structures), which may be either metal or hard plastic (if necessary to place the retractor under the patella itself). The blades come in two depths, shallow and deep. The metal lattice support is movable superior/inferior and medial/lateral to allow for adequate exposure. This also keeps the retractor in place while flexing and extending the knee.

FIG. 5D illustrates the distal femoral condyle replacement component or trial. There are three possibilities for the distal femoral condyle replacement:

1) Metal component with at least two pegs cemented into the distal femoral condyle;

2) Plastic component with at least two pegs cemented into the distal femoral condyle; and 3) Metal back component with at least two pegs cemented into the distal femoral condyle, with snap on plastic liners of various thicknesses.

The various steps and components discussed with respect to FIG. 1 are described in further detail below.

Pre-Operative Planning

As with any contemplated joint replacement, it is important that a comprehensive history pertaining to the patient's knee is obtained and a detailed physical exam of the knee is performed. Plain radiographs and an MRI need to be carefully evaluated. When considering a FCRA, there are important parameters to consider. No single one is absolutely definitive. These all need to be considered and discussed with the patient so he or she is involved in the decision making process (the art of medicine).

History

Where is the patient's pain located? If primarily around the involved compartment, an indication that FCRA may be indicated. If more diffuse and widespread, a FCRA may not be indicated.

When does it bother the patient? If primarily with weight bearing and/or going upstairs, more indicative of single compartment damage. If significantly present even without weight bearing, and when going downstairs, the damage may be more widespread and involve the patella and trochlea surfaces.

Does the knee give out with twisting activities? More likely damage to the weight bearing surface. Of course, there could be a localized meniscus tear without damage. Diagnostic testing will help determine this.

Physical Examination

Is there a deformity with weight bearing; genu varus with damage to the medical compartment, genu valgus with damage to the lateral compartment? Is there observed instability with ambulation? if so, these are a contraindication to a FCRA.

Is the pain confined to one compartment with palpation? The presence of pain to palpation to multiple compartments could indicate that there is more than one compartment damaged.

Is there substantial loss of range of motion? A loss of more than five degrees of full extension or flexion less than 125 is a relative contraindication for FCRA.

Is there ligamentous laxity? Mild apparent medial or lateral laxity is to be expected when a mild genu varus or genu *vagus* deformity is present. Substantial medial or lateral laxity, or anterior or posterior laxity, is contraindications to FCRA.

Are pain, crepitation, and mechanical findings confined to one weight bearing compartment with meniscal testing? If more than one compartment is involved, this may indicate that the FCRA is not appropriate, or there are bi-compartmental meniscus tears.

Plain Radiographs

A minimum of four views should be obtained: standing AP, standing PA, lateral, and the patellar trochlear view of the surgeon's choice (e.g. Houghston, sunrise, etc.).

The angle between the femur and tibia on the standing AP will need to be measured. While this can be measured on the computer screen of the electronic views, it is recommended that hard copies be obtained on any patient that FCRA is being considered. This will allow more accurate measurement be made to determine genu varus and genu valgus. A varus angle greater than five and a valgus angle greater than 8 is a relative contraindication to FCRA, as it suggests that instability may be present. If the contralateral knee is normal, that knee should be measured and compared to the knee being considered for FCRA.

The amount of narrowing and subchondral sclerosis needs to be determined on the standing radiographs. Both the standing AP and PA need to be evaluated to assure that only one of the weight bearing compartments is damaged. Narrowing, the genu angle, subchondral cysts, and subchondral sclerosis are all important to consider.

There are two specific areas to consider on the lateral view. The first is to determine if there are osteophytes at the superior and inferior pole of the patella, and the superior trochlea. If substantial, these osteophytes would indicate that there is patella trochlear damage and may be a contraindication to LRA. The second is to review the posterior condyle of the compartment being considered. The presence of osteophytes, subchondral cysts, and subchondral sclerosis would indicate that a traditional unicompartmental may be necessary.

The patella-trochlear view will need to be examined for two findings. The first is for substantial signs of degeneration: osteophytes, narrowing, subchondral cysts, and subchondral sclerosis. If substantial, the patient may require a total knee replacement. The second is for lateral patella tilt or subluxation. If the unicompartmental arthroplasty being considered is medial, and if a genu varus deformity is overorrected, this may lead to increased patella trochlear instability and degeneration, causing rapid failure and necessitating revision to a total knee.

After careful consideration of the patient's history, physical examination, and review of plain radiographs, a determination should be made if the patient is a possible candidate for FCRA. If the patient is determined to be a candidate, than an MRI should be obtained. (FIG. 1, Step 1A) There are six areas that specifically need to be scrutinized:

The patella and trochlea: The integrity of the subchondral bone and hyaline cartilage of each need to be determined. Substantial damage to either or both, especially when correlated with findings on the history and physical, would indicate a total knee or bicompartmental arthroplasty is indicated.

The opposite compartment: The integrity of the subchondral bone, the hyaline cartilage, and the meniscus need to be determined. If there is no significant damage to the compartment, yet the meniscus is torn, an arthroscopic meniscectomy on the opposite compartment will need to be performed at the same time as the FCRA.

The distal femoral condyle and underlying hyaline cartilage: Damage needs to be determined and confirmed.

The posterior femoral condyle and underlying hyaline cartilage: If not damaged, the distal femoral FCRA may be indicated. If substantial damage, than both the distal and posterior condyle will need replacement.

The meniscus of the involved compartment: If torn, than either arthmscopic or open partial meniscectomy will need to be performed at the time of the FCRA. (FIG. 1, Step 2).

Tibial plateau and overlying hyaline cartilage: If normal, than a FCRA could be indicated, after considering the history, the physical examination, review of the plain radiographs, and MRI.

Instrumentation

Intra-compartmental Insert (IC Insert): This has a curvilinear, pliable plastic surface that will be used for the FCRA procedure. The pliable plastic surface will not cause any damage to tibial articular surface, as opposed to a metal insert. It is 1.5 cm wide. The curvilinear plastic component will be placed in between the tibial and femoral articular surfaces, over the anterior meniscus. The handle of the IC Insert will be hard plastic or metal and will contain a hole for placement of the external alignment guide, if the surgeon's preference is such. (FIGS. 3A-3B).

External Alignment guide: If used, this will be inserted through the handle of the IC insert to check for AP and lateral alignment prior to fixation of the distal femoral cutting block to the proximal tibia, if the surgeon feels it is necessary to check this.

Distal femoral cutting block: This block will be attached to the IC Insert. Preferably, there will be neutral cutting slot. By slight angulation of the cutting block, e.g., 1 degree, 2 degree, or 3 degree superior slope, more or less of the distal condyle can be removed. This will allow a slight increased coverage if the distal femoral condyle wear extends slightly into the posterior condyle. However, unless otherwise determined, a neutral cut should be made. (FIGS. 4A-4B).

Figure 4C:
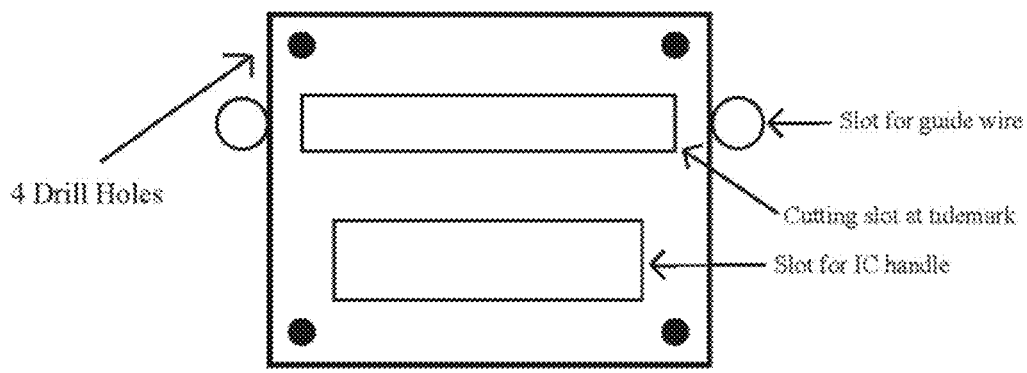
FIG. 4C is a schematic diagram depicting a front view of an alternate cutting block used in the method(s) and system(s) of present disclosure.
Figure 4D:
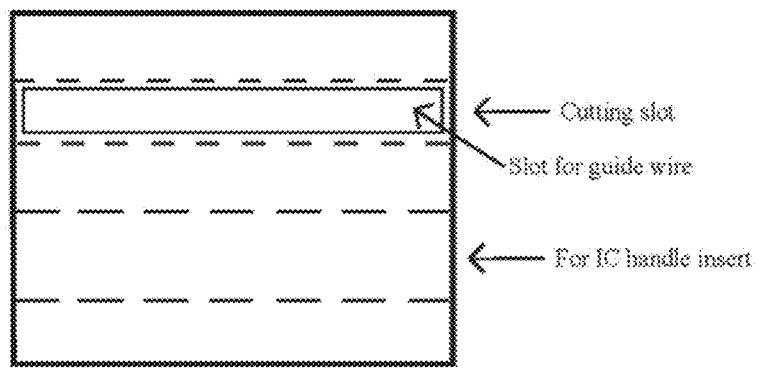
FIG. 4D is a schematic diagram depicting a side view of the alternate cutting block of FIG. 4C.
Figure 6:
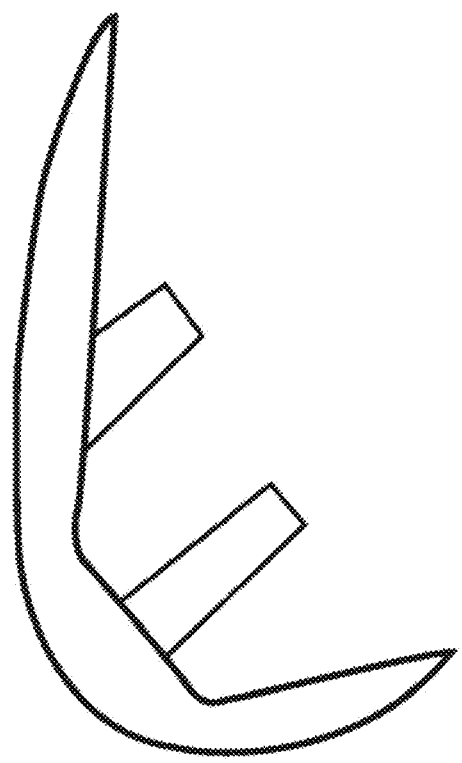
FIG. 6 is a schematic diagram of a distal and posterior femoral condyle trial.

Alternate distal femoral cutting block: This block will be attached to the IC Insert through the slot for the IC Handle. On each side of the block at the level of the cutting slot is a slot, preferably a round slot, for placement of a guidewire. This guidewire will be placed against the bone of the femoral condyle to be cut. The surgeon will use this to assure the proper distal femoral cut. One of the unique functions and advantages due to the flexibility imparted by the plastic material of the IC Insert is that once the femoral cutting block is place over the IC Insert handle, the surgeon is able to change the position of the femoral cutting block once aligned with the guide wire placed in its slot. This assures the correct distal femoral cut. The distal femoral cutting block is then pinned into place prior to making the distal femoral cut. (FIGS. 4C-4D).

FCRA (Box) retractor: This is a retractor designed specifically for the FCRA procedure. Since the incision only needs to expose the most inferior aspect of the distal femur and most superior aspect of the tibia, it may be relatively small. However, the patella, the patellar and quadriceps tendon, and the opposite capsular structures must be retracted to allow placement of the instruments and allow visualization of the bone cuts, trial sizing, and then placement of the definitive component. There are four right angle blades (two for medial structures and two for lateral structures), which may be either metal or hard plastic (if necessary to place the retractor under the patella itself). The blades come in two depths, shallow and deep. The metal lattice support is movable superior/inferior and medial/lateral to allow for adequate exposure. This also keeps the retractor in place while flexing and extending the knee while assessing the component. (FIG. 2A-2C).

Components

Finite Element Analysis defines the function of the knee to be one of various contact points between structures of different mesh densities. (Pfeiffer, F. M., Volume 29, Number 2, 2106. *The Journal of Knee Surgery*.) The knee weight bearing areas consist of three structures of different densities, bone (rigid, the distal femur and proximal tibia), hyaline cartilage (semi-rigid, the femoral and tibial articular surfaces) and the meniscus (soft, the medial and lateral meniscus).

Traditional Uni-compartment and total knee replacement has evolved so that a rigid surface (the femoral component) articulates with a semi-rigid surface (the polyethylene) liner of the tibia and the polyethylene patella component). This has worked well over the years and remains the mainstay of knee replacement arthroplasty.

However, observed during arthroscopic surgery on the knee, often times there exists a partial meniscus tear, which in turn has damaged substantially the corresponding gliding surface of the distal and/or posterior femoral hyaline cartilage, while leaving the tibial hyaline cartilage normal. Currently, arthroscopic debridement of the damaged femoral articular surface and removal of the torn meniscus is all that can be offered from a mechanical standpoint to help these patients. Hyaluronidase injections, anti-inflammatory medications, knee supports, and orthotics can sometimes help these patients. Commonly, the compartment involved in these patients quickly deteriorates to where a Uni-compartment arthroplasty becomes necessary.

Since the tibial articular surface is essentially undamaged and much of the meniscus remains intact, the basic geometry of the compartment is normal, except for the damage to the femoral gliding surface. Accordingly, the presently disclosed method(s) would not replace the entire compartment. The presently disclosed method(s) would just replace the damaged distal femoral hyaline surface, while leaving the tibial articular surface and undamaged meniscal tissue intact.

Since the hyaline cartilage surface is a semi-rigid surface, replacing it with a rigid surface (the current metal surfaces being used) would be expected to cause progressive damage to the tibial hyaline surface. It would be more physiologically compatible to replace it with a less rigid surface. That way, the semi-rigid against semi-rigid surface of the normal hyaline cartilage would be preserved. The "plastic deformation" that occurs in the femoral articular surface at the junction of trochlea and the distal femoral condyle, is the so called "tide-mark." These are semi-rigid surfaces, not rigid surfaces.

Currently, with today's materials, the replacement of the distal femoral condyle should be a polyethylene component. That way, two semi-rigid surfaces would be articulating (i.e. polyethylene femoral condyle and native tibial hyaline cartilage), rather than a semi-rigid surface (native tibial hyaline cartilage) against a rigid surface (metal distal femoral component).

There are three embodiments for the femoral condyle replacement, whether the distal femoral condyle or both the distal and posterior femoral condyles. Preferably a polyethylene component with at least two pegs for cement fixation into the femur is used. A second, alternative component will be a metal back component with at least two pegs cemented into the femur with snap on polyethylene liners of various thicknesses. The third embodiment is a metal component with at least two pegs cemented into the distal femur.

FCRA Surgical Technique

An arthroscopic procedure may first be performed. If necessary, a partial meniscectomy will need to be performed. (FIG. 1, step 2). It is unusual that there will be a significant amount of damage to the distal femoral condyle to warrant a FCRA without meniscal tearing. Whether performed arthroscopically or as part of the open procedure, the remaining meniscus need to be well-balanced and stable, especially posteriorly. Steps 1A and 2 may previously have been performed by an Arthroscopist who refers the patient for the FCRA. (FIG. 1, Step 1B).

If an arthroscopy is performed first, arthroscopic portal on the side having the open procedure may be vertical, and closer to the midline than what the surgeon is used to. This will allow the arthroscopic incision to be incorporated into the open procedure. Of course, this depends on where the surgeon normally makes his or her portal. However, if the surgeon prefers a horizontal incision, made slightly medially or laterally to the midline, that is very acceptable.

After a decision to proceed with the FCRA is made (FIG. 1, Step 3), a small vertical arthrotomy incision (which would be approximately 2-3 inches) is made slightly medially or laterally to the patellar tendon, depending on what compartment is involved. (FIG. 1, step 4) The box retractor is positioned (FIGS. 2A-2C). As with any surgical technique, the incision needs to be long enough to allow adequate visualization. Initially, it is recommended that the incision be made longer, and then may be shortened as the surgeon gains confidence in the procedure.

The "tide mark" is checked and marked with the knee in its full extension. With the knee remaining in extension, a slight valgus stress (for medial compartment) or varus stress (for lateral compartment) is imparted and the pliable plastic portion of the IC insert (FIGS. 3A-3B) is then inserted over the anterior third of the meniscus in between the distal femoral condyle and tibial plateau. (FIG. 1, Step 5). The anterior meniscus usually sits slightly inferior to the medial tibial articular surface and is pliable enough to normally allow the IC Insert to be placed into the medial compartment without difficulty. In unusual cases where the IC Insert cannot be placed over the anterior meniscus, the anterior meniscus can be incised at this time and repaired at the end of the case.

The femoral cutting block (FIGS. 4A-4B) is attached to the IC Insert, making sure the cutting slot aligns with the tide mark, and is then affixed with two pins into the distal femur. (FIG. 1, Step 6) If surgeon preference, the external alignment guide is then inserted through the metal handle of the IC Insert and the AP, lateral, and rotational planes are checked. It is important not to place the IC Insert against the tibial spine, as this will cause external rotation of the cutting blocks. However, since the tibial articular surface is not being resected, rotation of the implanted femoral component will be determined prior to cementing. The external alignment guide may not be necessary.

Once alignment and rotation is confirmed, the distal femoral cutting block is pinned to the tibia. This allows secure fixation. The distal femoral is then cut. (FIG. 1, Step 7) If the posterior condyle is also to be removed, the surgeon will use his or her standard system for the posterior and chamfer cuts. (FIG. 1, Steps 8B and 10).

All the instrumentation is now removed. The trial components are tried until the proper size is determined. (FIGS. 5A-5C and 5D or 6). It is important that trial component is not proud either anterior or posterior, but rather are recessed. If proud anteriorly, this can cause impingement on the patella. If proud posteriorly, this can cause impingement on the posterior meniscus (if saved, or on the posterior tibial articular surface if not. The knee is put through a ROM to make sure there is not impingement anteriorly or posteriorly.

The fixation posts are then drilled after confirmation of proper size, motion, and setting of the trial is confirmed. (FIG. 1, Step 9 or 10). The distal femoral component (FIG. 1, Step 9; and FIG. 5D) or the distal and posterior femoral condyle trial (FIG. 1, Step 10; and FIG. 6) is then cemented into place. Excess cement is removed after the cement hardens. Again, a check is made to assure no impingement.

The knee is irrigated, tourniquet released if used, and hemostasis obtained. The surgeon will need to determine if a drain is necessary. No immobilization is required unless preferred by the surgeon.

While the embodiment(s) disclosed herein are illustrative of the structure, function and operation of the exemplary method(s), system(s), component(s) and device(s), it should be understood that various modifications may be made thereto with departing from the teachings herein. Further, the components of the method(s), system(s), component(s) and device(s) disclosed herein can take any suitable form, including any suitable components capable of adequately performing their respective intended functions, as may be known in the art.

While the foregoing discussion presents the teachings in an exemplary fashion with respect to the disclosed method(s), system(s), component(s) and device(s) for femoral condylar resection arthroplasty of the knee, it will be apparent to those skilled in the art that the present disclosure may apply to other arthroscopic and/or arthroplasty surgical method(s) and system(s). Further, while the foregoing has described what are considered to be the best mode and/or other examples, it is understood that various modifications may be made therein and that the subject matter disclosed herein may be implemented in various forms and examples, and that the method(s), system(s), component(s) and device(s) may be applied in numerous applications, only some of which have been described herein.

What is claimed is:

1. A system for femoral condylar resection arthroplasty of the knee, comprising:
    a box retractor having a metal lattice support;
    a flexible intercondylar insert comprising a pliable plastic;
    a distal femoral condyle culling block, wherein the distal femoral condyle cutting block eludes at least one guidewire slot; and
    a distal femoral condyle trial.

2. The system of claim 1, further comprising a posterior and chamfer cutting block.

3. The system of claim 2, wherein the distal femoral condyle trial comprises a distal and posterior femoral condyle to trial.

4. The system of claim 1, wherein the intercondylar insert is 1.5 cm wide.

5. The system of claim 1, wherein the intercondylar insert has a curvilinear, pliable plastic surface.

6. The system of claim 1, wherein the intercondylar insert includes a handle.

7. The system of claim 6, wherein the handle contains a hole for placement of an external alignment guide.

8. The system of claim 1, wherein the metal lattice support is adapted to provide for adjustable exposure of a knee joint.

* * * * *